(12) United States Patent
Ignatyev et al.

(10) Patent No.: US 7,652,171 B2
(45) Date of Patent: Jan. 26, 2010

(54) CLEAVAGE OF DIALKOXYALKANES IN IONIC LIQUIDS

(75) Inventors: Nikolai (Mykola) Ignatyev, Duisburg (DE); Karsten Koppe, Marl (DE); Hermann Josef Frohn, Kempen (DE); Peter Barthen, Rheinberg (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 12/280,390

(22) PCT Filed: Jan. 25, 2007

(86) PCT No.: PCT/EP2007/000633

§ 371 (c)(1),
(2), (4) Date: Aug. 22, 2008

(87) PCT Pub. No.: WO2007/104380

PCT Pub. Date: Sep. 20, 2007

(65) Prior Publication Data

US 2009/0012329 A1  Jan. 8, 2009

(30) Foreign Application Priority Data

Feb. 23, 2006  (DE) .................. 10 2006 008 424

(51) Int. Cl.
*C07C 45/59* (2006.01)
*C07C 45/55* (2006.01)

(52) U.S. Cl. .............. 568/361; 568/386; 568/405; 568/483

(58) Field of Classification Search .............. 568/361, 568/386, 405, 483
See application file for complete search history.

(56) References Cited

U.S. PATENT DOCUMENTS 4,161,614 A  7/1979  Konz et al.

OTHER PUBLICATIONS

Driver et al. 3-Methylimidazolium bromhydrogenates(I): a room temperature ionic liquid for ether cleavage. Green Chemistry, 2003, vol. 5, pp. 163-169.*
Dalpozzo et al. Simple and Effective Chemoselective Mild Deprotection of Acetals and Ketals using Cerium (III) Triflate. Journal of Organic Chemistry, 2002, vol. 67 (25), pp. 9093-9095.*

* cited by examiner

*Primary Examiner*—Sikarl A Witherspoon
(74) *Attorney, Agent, or Firm*—Millen, White, Zelano, Branigan, P.C.

(57) ABSTRACT

The present invention relates to a process for the cleavage of dialkoxyalkanes to give corresponding aldehydes or ketones, where the cleavage is carried out in the presence of at least one ionic liquid of the general formula $K^+A^-$.

8 Claims, No Drawings

CLEAVAGE OF DIALKOXYALKANES IN IONIC LIQUIDS

The present invention relates to a process for the cleavage of dialkoxyalkanes to give corresponding aldehydes or ketones, where the cleavage is carried out in the presence of at least one ionic liquid of the general formula $K^+A^-$.

Carbonyl groups are a regular constituent of organic compounds, for example of pharmaceutical active compounds, crop-protection agents, polymers or precursors in fine chemistry. During the synthesis, it is frequently necessary to protect the carbonyl groups by a corresponding protecting group in order to be able to carry out further modifications on the respective compound, for example by reaction with organometallic reagents which would react with the carbonyl group in a side reaction.

Ketals and acetals have become established as the standard protecting group for carbonyl functions of aldehydes and ketones. These are dialkoxyalkanes, which are obtained from the corresponding carbonyl compounds by reaction with alcohols. These geminal diethers are unreactive to a number of reagents, for example organometallic reagents. If required, the carbonyl groups can be restored by cleavage of the ketals or acetals with liberation of corresponding alcohols. The cleavage of the dialkoxyalkanes is usually carried out by reaction with acids, as described, for example, in A. Streitwieser, C. H. Heathcock, E. M. Kosover, Organische Chemie [Organic Chemistry], 2nd Edition, VCH, Weinheim 1994, 402-403. To this end, mineral acids or strong organic acids, such as, for example, p-toluenesulfonic acid, are usually employed. This reaction is carried out in organic solvents, which have to be separated off from the desired carbonyl compound together with the by-products after the reaction. However, the use of organic solvents and strong acids proves to be disadvantageous, in particular in large-scale industrial processes, since large amounts of solvents, some of which are mixed with strong acids, have to be disposed of. For large-scale industrial syntheses in particular, the said methods thus prove to be disadvantageous since, in particular on use of solvents, additional safety aspects for preventing environmental pollution and for fire protection have to be taken into account.

There is thus a demand for alternatives for the cleavage of dialkoxyalkanes with liberation of the corresponding aldehydes or ketones, which are simple to carry out, give a high yield of the corresponding aldehydes and ketones and at the same time avoid the use of large amounts of solvents.

Accordingly, the object of the present invention is to provide a process which meets the above-mentioned requirements, is readily controllable, does not have great safety demands and thus also allows economical cleavage of ketals or acetals on a commercial scale. Surprisingly, it has been found that ionic liquids are ideally suitable as alternative solvent for the cleavage of dialkoxyalkanes.

The present invention accordingly relates to a process for the cleavage of dialkoxyalkanes of the general formula (I) to give aldehydes or ketones:

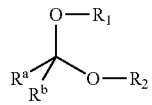

I where
$R^a$ and $R^b$, independently of one another, denote an optionally substituted aliphatic or aromatic radical, which may have one or more heteroatoms, where one of the radicals $R^a$ or $R^b$ may also denote H, and where the two radicals $R^a$ and $R^b$ may be connected to one another, and where $R_1$ and $R_2$, independently of one another, denote an optionally substituted saturated or unsaturated aliphatic or aromatic radical, which may have one or more heteroatoms, and where the two radicals $R_1$ and $R_2$ may be connected to one another, characterised in that the cleavage is carried out in the presence of at least one ionic liquid of the general formula $K^+A^-$. It has been found that ionic liquids are particularly suitable for carrying out the cleavage of dialkoxyalkanes. When carrying out the process according to the invention, the at least one ionic liquid can be in the form of a mixture with further solvents, in particular organic solvents, with the process preferably being carried out without addition of a further solvent, i.e. solely in the presence of at least one ionic liquid.

Ionic liquids or liquid salts are ionic species which consist of an organic cation ($K^+$) and a generally inorganic anion ($A^-$). They do not contain any neutral molecules and usually have melting points below 373 K.

Intensive research is currently being carried out in the area of ionic liquids since the potential applications are multifarious. Review articles on ionic liquids are, for example, R. Sheldon "Catalytic reactions in ionic liquids", Chem. Commun., 2001, 2399-2407; M. J. Earle, K. R. Seddon "Ionic liquids. Green solvent for the future", Pure Appl. Chem., 72 (2000), 1391-1398; P. Wasserscheid, W. Keim "Ionische Flüssigkeiten—neue Lösungen für die Übergangsmetallkatalyse" [Ionic Liquids—Novel Solutions for Transition-Metal Catalysis], Angew. Chem., 112 (2000), 3926-3945; T. Welton "Room temperature ionic liquids. Solvents for synthesis and catalysis", Chem. Rev., 92 (1999), 2071-2083 or R. Hagiwara, Ya. Ito "Room temperature ionic liquids of alkylimidazolium cations and fluoroanions", J. Fluorine Chem., 105 (2000), 221-227.

Since ionic liquids are salts, they have no volatility and thus also do not liberate any flammable or toxic vapours. They thus represent a safe medium for carrying out the ketal cleavage. In addition, it has been found that, on use of ionic liquids for the cleavage of dialkoxyalkanes, the addition of acid which is otherwise usual for catalysing the reaction is not absolutely necessary. The ionic liquid itself can thus catalyse the desired re-liberation of the carbonyl function. In the simplest case, the aldehyde or ketone obtained can be decanted off from the ionic liquid and employed further without further purification. The ionic liquid too can be recycled simply in this manner and can be re-used a number of times. Overall, the process according to the invention proves to be a simple and inexpensive process which is also suitable for synthesis on a commercial scale.

Suitable dialkoxyalkanes are those of the formula (I)

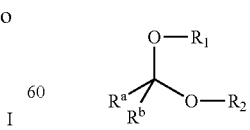

I where
$R^a$ and $R^b$, independently of one another, denote an optionally substituted aliphatic radical or aromatic radical, which may have one or more heteroatoms, where one of the radicals $R^a$ or $R^b$ may also denote H, and where the two radicals $R^a$ and $R^b$ may be connected to one another, and where $R_1$ and $R_2$, independently of one another, denote an optionally substituted saturated or unsaturated aliphatic or aromatic radical, which may have one or more heteroatoms, and where the two radicals $R_1$ and $R_2$ may be connected to one another.

$R_1$ and $R_2$ may, independently of one another, be saturated or unsaturated aliphatic radicals or aromatic radicals. Suitable aliphatic radicals are preferably straight-chain or branched alkyl groups having 1 to 10 C atoms, in particular $R_1$ and $R_2$ are each, independently of one another, methyl, ethyl, n-propyl, isopropyl, n-butyl, tert-butyl, sec-butyl, phenyl or cyclohexyl, very particularly preferably methyl, ethyl, n-propyl, isopropyl or n-butyl. Suitable aromatic radicals are, for example, phenyl and benzyl.

The radicals $R^a$ and $R^b$ as well as $R_1$ and $R_2$ are preferably connected to one another, for example with formation of an aliphatic and/or aromatic ring or fused ring system, which may also have one or more heteroatoms.

$R_1$ and $R_2$ are very particularly preferably connected to one another with formation of an aliphatic saturated or unsaturated ring, i.e. $R_1$ and $R_2$ together form a saturated or unsaturated alkyl chain, where the alkyl chain can have 1 to 10 C atoms. The alkyl chain preferably has 2 to 5 C atoms, overall giving a dialkoxyalkane having a 5- to 8-membered ring. The alkyl chain very particularly preferably has 2 C atoms, giving a dialkoxyalkane having a 5-membered ring. These particularly preferred dialkoxyalkanes are obtained by reaction of the corresponding carbonyl compound with 1,2-ethanediol. The formation of a five-membered ring is particularly favoured here and therefore preferred.

$R^a$ preferably has a meaning in accordance with formula Ia

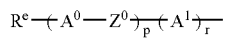

Ia in which $R^e$ denotes an alkyl radical having 1 to 15 C atoms which is unsubstituted, mono- or polysubstituted by CN and/or halogen, where, in addition, one or more $CH_2$ groups in these radicals may be replaced by —O—, —S—, —CH=CH—, —C≡C—, —OC—O— and/or —O—CO—, and/or, in addition, one or more CH groups may be replaced by N or P in such a way that two O atoms are not linked directly to one another, or, if r and/or p are different from 0, also denotes H, halogen, CN, $SF_5$ or NCS, $A^0$, $A^1$ each, independently of one another, denote
  a) a 1,4-cyclohexenylene or 1,4-cyclohexylene radical, in which one or two non-adjacent $CH_2$ groups may be replaced by —O— or —S—,
  b) a 1,4-phenylene radical, in which one or two CH groups may be replaced by N,
  c) a radical from the group piperidine-1,4-diyl, 1,4-bicyclo-[2.2.2]octylene, phenanthrene-2,7-diyl, naphthalene-2,6-diyl, decahydronaphthalene-2,6-diyl and 1,2,3,4-tetrahydronaphthalene-2,6-diyl,
  d) a divalent radical from the group furan, pyrrole, thiophene, pyrazole, imidazole, 1,2-oxazole, 1,3-oxazole, thiazole, pyridine, pyridazine, pyrimidine, pyrazine, 2H-pyran, 4H-pyran, purine, pteridine, 1H-azepine, 3H-1,4-diazepine, indole, benzofuran, benzothiophene, quinoline, isoquinoline, phenazine, phenoxazine, phenothiazine and 1,4-benzodiazepine, where the radicals a), b), c) and d) may be mono- or polysubstituted by $R^e$, in particular by halogen and/or CN, $Z^0$ denotes —CO—O—, —O—CO—, —$CF_2$O—, —$OCF_2$—, —$CH_2$O—, —$OCH_2$—, —$CH_2CH_2$—, —$(CH_2)_4$—, —$C_2F_4$—, —$CH_2CF_2$—, —$CF_2CH_2$—, —CF=CF—, —CH=CH—, —C≡C— or a single bond, p denotes 0, 1, 2 or 3, and r denotes 0, 1 or 2.

Preferred meanings of $R^e$ are straight-chain or branched alkyl and alkoxy radicals having 1 to 8 C atoms, which may be monosubstituted by —CN and/or mono- or polysubstituted by halogen.

Preferred meanings of $A^0$ and/or $A^1$ are 1,4-cyclohexylene, in which one or two non-adjacent $CH_2$ groups may be replaced by —O—, 1,4-phenylene, in which one or two CH groups may be replaced by N, phenanthrene-2,7-diyl, naphthalene-2,6-diyl, decahydronaphthalene-2,6-diyl and 1,2,3,4-tetrahydronaphthalene-2,6-diyl, where these radicals may be mono- or polysubstituted by halogen, in particular fluorine and/or chlorine, CN and/or optionally halogen-substituted $C_{1-5}$-alkyl or -alkoxy.

$R^a$ may also be a constituent of a ligand, for example a cyclopentadienyl system in an organometallic complex.

Particularly preferred groups $R^a$ are shown below:

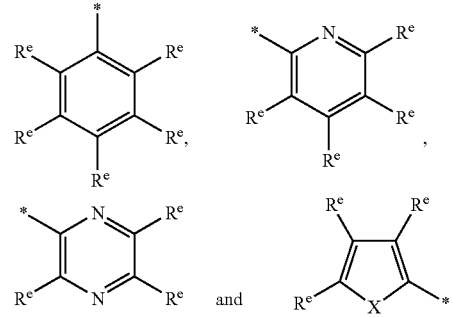

in which X denotes O, $NR^e$ or S, $R^e$ has the meaning indicated, and * indicates the free bond.

Above and below, halogen as substituent of organic radicals denotes fluorine, chlorine, bromine or iodine, preferably fluorine or chlorine, particularly preferably fluorine.

Above and below, groups and substituents which occur more than once, such as, for example, $A^0$, $Z^0$, $A^1$, $R^e$, may in each case have identical or different meanings.

The radical $R^a$ preferably has a meaning in accordance with the formula Ia and the other radical $R^b$ denotes H.

$R^a$ and $R^b$ are furthermore preferably connected to one another in such a way that the dialkoxy compound of the formula I has a meaning in accordance with formula Ib:

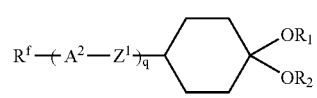

Ib in which $R^f$ has one of the meanings indicated for $R^e$, $A^2$ has one of the meanings indicated for $A^0$, $A^1$, $Z^1$ has one of the meanings indicated for $Z^0$, q denotes 0, 1, 2 or 3, and $R_1$ and $R_2$ have the meanings indicated above and below.

The ionic liquids of the general formula $K^+A^-$ are essential for the process according to the invention for the cleavage of dialkoxyalkanes. The choice of the anion $A^-$ of the ionic liquid plays a particular role here. The anion $A^-$ is preferably an anion of a corresponding strong acid. In particular, the anion $A^-$ of the ionic liquid is selected from the group $[HSO_4]^-$, $[SO_4]^{2-}$, $[NO_3]^-$, $[BF_4]^-$, $[(R_F)BF_3]^-$, $[(R_F)_2BF_2]^-$, $[(R_F)_3BF]^-$, $[(R_F)_4B]^-$, $[B(CN)_4]^-$, $[PO_4]^{3-}$, $[HPO_4]^{2-}$, $[H_2PO_4]^-$, $[alkyl\text{-}OPO_3]^{2-}$, $[(alkyl\text{-}O)_2PO_2]^-$, $[alkyl\text{-}PO_3]^{2-}$, $[R_FPO_3]^{2-}$, $[(alkyl)_2PO_2]^-$, $[(R_F)_2PO_2]^-$, $[R_FSO_3]^-$, $[HOSO_2(CF_2)_nSO_2O]^-$, $[OSO_2(CF_2)_nSO_2O]^{2-}$, $[alkyl\text{-}SO_3]^-$, $[HOSO_2(CH_2)_nSO_2O]^-$, $[OSO_2(CH_2)_nSO_2O]^{2-}$, $[alkyl\text{-}OSO_3]^-$, $[alkyl\text{-}C(O)O]^-$, $[HO(O)C(CH_2)_nC(O)O]^-$, $[R_FC(O)O]^-$, $[HO(O)C(CF_2)_nC(O)O]^-$, $[O(O)C(CF_2)_nC(O)O]^{2-}$, $[(R_FSO_2)_2N]^-$, $[(FSO_2)_2N]^-$, $[((R_F)_2P(O))_2N]^-$, $[(R_FSO_2)_3C]^-$, $[(FSO_2)_3C]^-$, $Cl^-$ and/or $Br^-$, where n=1 to 8, $R_F$ has the meaning of fluorinated alkyl $(C_mF_{2m-x+1}H_x)$ where m=1-12 and x=0-7, where, for m=1, x must be 0 to 2, and/or fluorinated (also perfluorinated) aryl or alkylaryl.

The alkyl group in the above-mentioned anions can be selected from straight-chain or branched alkyl groups having 1 to 20 C atoms, preferably having 1 to 14 C atoms and particularly preferably having 1 to 4 C atoms.

$R_F$ preferably denotes $CF_3$, $C_2F_5$, $C_3F_7$ or $C_4F_9$.

There are no restrictions per se with respect to the choice of the cation $K^+$ of the ionic liquid. However, preference is given to organic cations, particularly preferably ammonium, phosphonium, thiouronium, guanidinium or heterocyclic cations.

Ammonium cations can be described, for example, by the formula (1)

$$[NR_4]^+ \quad (1),$$

where

R in each case, independently of one another, denotes H, where all substituents R cannot simultaneously be H, straight-chain or branched alkyl having 1-20 C atoms, straight-chain or branched alkenyl having 2-20 C atoms and one or more non-conjugated double bonds, straight-chain or branched alkynyl having 2-20 C atoms and one or more non-conjugated triple bonds, a saturated, partially or fully unsaturated cycloaliphatic radical having 3-7 C atoms, which may be substituted by alkyl groups having 1-6 C atoms, where one or more R may be partially or fully substituted by halogens, in particular —F and/or —Cl, or partially by —OR', —CN, —C(O)OH, —C(O)NR'$_2$, —SO$_2$NR'$_2$, —SO$_2$OH, —SO$_2$X or —NO$_2$, and where one or two non-adjacent carbon atoms in R which are not in the α-position may be replaced by atoms and/or atom groups selected from the group —O—, —S—, —S(O)—, —SO$_2$—, —N$^+$R'$_2$—, —C(O)NR'—, —SO$_2$NR'— or —P(O)R'—, where R' may be H, non-, partially or perfluorinated C$_1$- to C$_6$-alkyl, C$_3$- to C$_7$-cycloalkyl, or unsubstituted or substituted phenyl, and X may be halogen.

Phosphonium cations can be described, for example, by the formula (2)

$$[PR^2_4]^+ \quad (2),$$

where $R^2$ in each case, independently of one another, denotes H, NR'$_2$, straight-chain or branched alkyl having 1-20 C atoms, straight-chain or branched alkenyl having 2-20 C atoms and one or more non-conjugated double bonds, straight-chain or branched alkynyl having 2-20 C atoms and one or more non-conjugated triple bonds, a saturated, partially or fully unsaturated cycloaliphatic radical having 3-7 C atoms, which may be substituted by alkyl groups having 1-6 C atoms, where one or more $R^2$ may be partially or fully substituted by halogens, in particular —F and/or —Cl, or partially by —OR', —CN, —C(O)OH, —C(O)NR'$_2$, —SO$_2$NR'$_2$, —SO$_2$OH, —SO$_2$X or —NO$_2$, and where one or two non-adjacent carbon atoms in $R^2$ which are not in the α-position may be replaced by atoms and/or atom groups selected from the group —O—, —S—, —S(O)—, —SO$_2$—, —N$^+$R'$_2$—, —C(O)NR'—, —SO$_2$NR'— or —P(O)R'—, where R'=H, non-, partially or perfluorinated C$_1$- to C$_6$-alkyl, C$_3$- to C$_7$-cycloalkyl, or unsubstituted or substituted phenyl, and X=halogen.

However, cations of the formulae (1) and (2) in which all four or three substituents R and $R^2$ are fully substituted by halogens are excluded, for example the tris(trifluoromethyl) methylammonium cation, the tetra(trifluoromethyl)ammonium cation or the tetra(nonafluorobutyl)ammonium cation.

Suitable thiouronium cations can be described by the formula (3)

$$[(R^3R^4N)\!\!=\!\!C(\!=\!\!SR^5)(NR^6R^7)]^+ \quad (3),$$

where $R^3$ to $R^7$ each, independently of one another, denote hydrogen, straight-chain or branched alkyl having 1 to 20 C atoms, straight-chain or branched alkenyl having 2-20 C atoms and one or more non-conjugated double bonds, straight-chain or branched alkynyl having 2-20 C atoms and one or more non-conjugated triple bonds, a saturated, partially or fully unsaturated cycloaliphatic radical having 3-7 C atoms, which may be substituted by alkyl groups having 1-6 C atoms, where one or more of the substituents $R^3$ to $R^7$ may be partially or fully substituted by halogens, in particular —F and/or —Cl, or partially by —OH, —OR', —CN, —C(O)OH, —C(O)NR'$_2$, —SO$_2$NR'$_2$, —SO$_2$OH, —SO$_2$X or —NO$_2$, and where one or two non-adjacent carbon atoms in $R^3$ to $R^7$ which are not in the α-position may be replaced by atoms and/or atom groups selected from the group —O—, —S—, —S(O)—, —SO$_2$—, —N$^+$R'$_2$—, —C(O)NR'—, —SO$_2$NR'— or —P(O)R'—, where R'=H, non-, partially or perfluorinated C$_1$- to C$_6$-alkyl, C$_3$- to C$_7$-cycloalkyl, or unsubstituted or substituted phenyl, and X=halogen.

Guanidinium cations can be described by the formula (4)

$$[C(NR^8R^9)(NR^{10}R^{11})(NR^{12}R^{13})]^+ \quad (4),$$

where $R^8$ to $R^{13}$ each, independently of one another, denote hydrogen, —CN, NR'$_2$, straight-chain or branched alkyl having 1 to 20 C atoms, straight-chain or branched alkenyl having 2-20 C atoms and one or more non-conjugated double bonds, straight-chain or branched alkynyl having 2-20 C atoms and one or more non-conjugated triple bonds, a saturated, partially or fully unsaturated cycloaliphatic radical having 3-7 C atoms, which may be substituted by alkyl groups having 1-6 C atoms, where one or more of the substituents $R^8$ to $R^{13}$ may be partially or fully substituted by halogens, in particular —F and/or —Cl, or partially by —OR', —CN, —C(O)OH, —C(O)NR'$_2$, —SO$_2$NR'$_2$, —SO$_2$OH, —SO$_2$X or —NO$_2$, and where one or two non-adjacent carbon atoms in $R^8$ to $R^{13}$ which are not in the α-position may be replaced by atoms and/or atom groups selected from the group —O—, —S—, —S(O)—, —SO$_2$—, —N$^+$R'$_2$—, —C(O)NR'—, —SO$_2$NR'— or —P(O)R'—, where R'=H, non-, partially or perfluorinated C$_1$- to C$_6$-alkyl, C$_3$- to C$_7$-cycloalkyl, or unsubstituted or substituted phenyl, and X=halogen.

In addition, it is possible to employ cations of the general formula (5)

[HetN]$^+$ (5), where

HetN$^+$ denotes a heterocyclic cation selected from the group

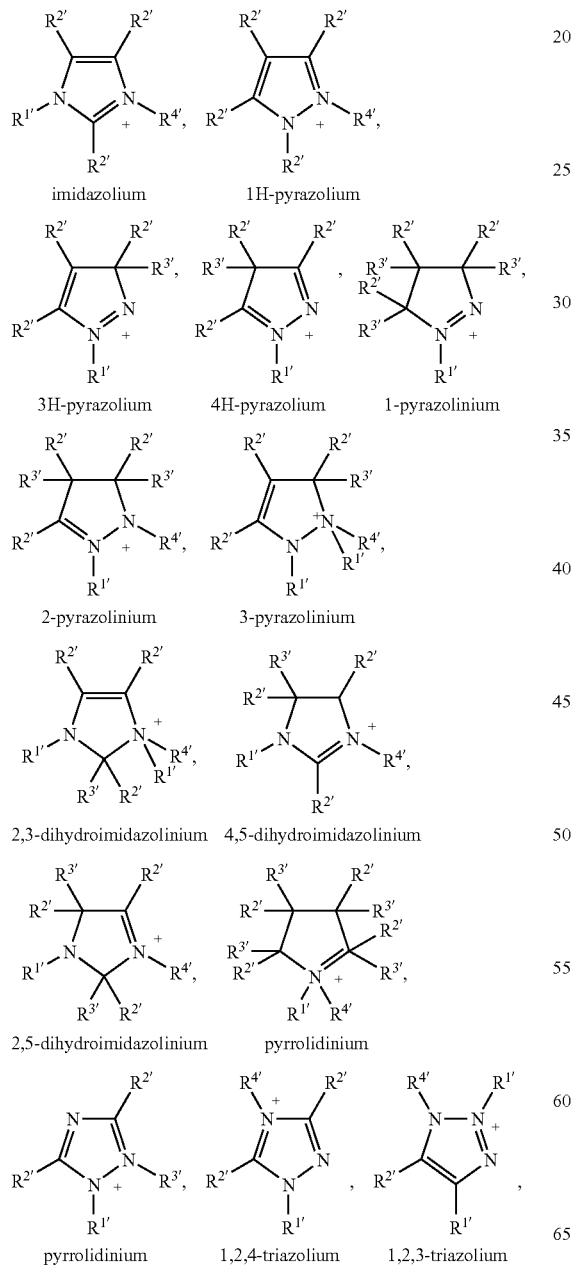

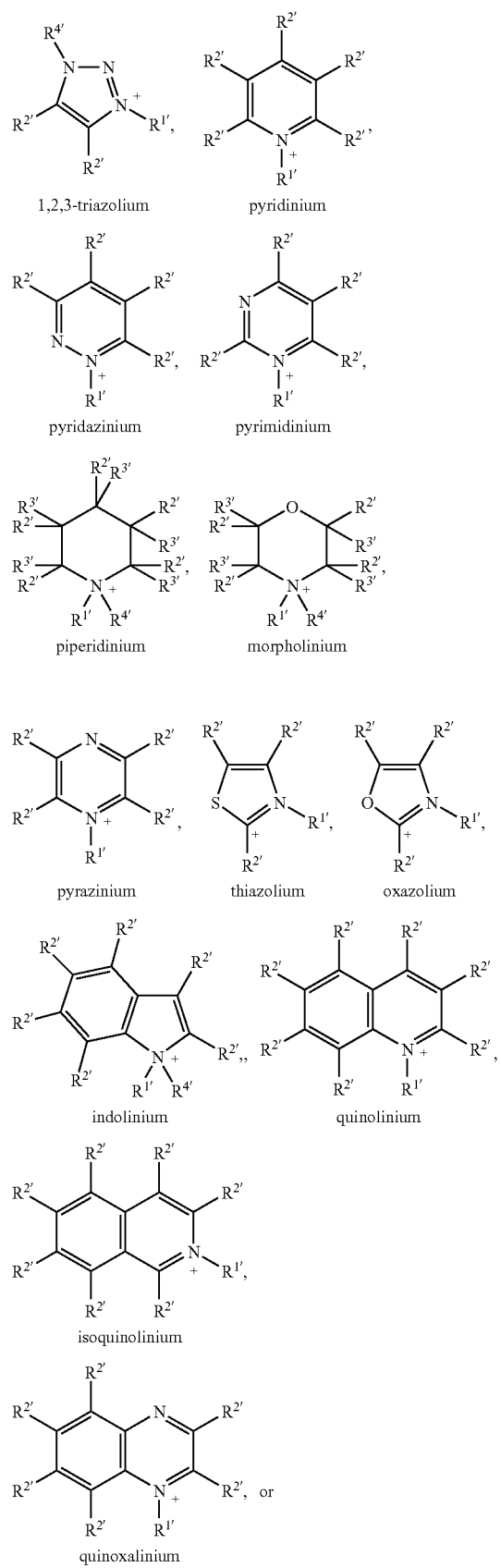

-continued

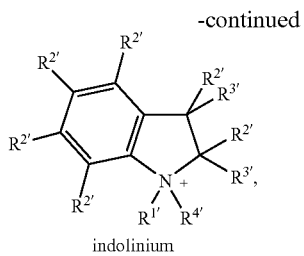

indolinium where the substituents $R^1$ to $R^4$ each, independently of one another, denote hydrogen, —CN, straight-chain or branched alkyl having 1-20 C atoms, straight-chain or branched alkenyl having 2-20 C atoms and one or more non-conjugated double bonds, straight-chain or branched alkynyl having 2-20 C atoms and one or more non-conjugated triple bonds, a saturated, partially or fully unsaturated cycloaliphatic radical having 3-7 C atoms, which may be substituted by alkyl groups having 1-6 C atoms, saturated, partially or fully unsaturated heteroaryl, heteroaryl-$C_1$-$C_6$-alkyl or aryl-$C_1$-$C_6$-alkyl, where the substituents $R^{1'}$, $R^{2'}$, $R^{3'}$ and/or $R^{4'}$ together may also form a ring system, where one or more substituents $R^{1'}$ to $R^{4'}$ may be partially or fully substituted by halogens, in particular —F and/or —Cl, or —OR', —CN, —C(O)OH, —C(O)NR'$_2$, —SO$_2$NR'$_2$, —C(O)X, —SO$_2$OH, —SO$_2$X or —NO$_2$, but where $R^{1'}$ and $R^{4'}$ cannot simultaneously be fully substituted by halogens, and where, in the substituents $R^{1'}$ to $R^{4'}$, one or two non-adjacent carbon atoms which are not bonded to the heteroatom may be replaced by atoms and/or atom groups selected from —O—, —S—, —S(O)—, —SO$_2$—, —N$^+$R'$_2$—, —C(O)NR'—, —SO$_2$NR'— or —P(O)R'—, where R'=H, non-, partially or perfluorinated $C_1$- to $C_6$-alkyl, $C_3$- to $C_7$-cycloalkyl, or unsubstituted or substituted phenyl, and X=halogen.

Suitable as substituent $R^{2'}$ are, in particular, also atom groups selected from —OR', —NR'$_2$, —C(O)OH, —C(O)NR'$_2$, —SO$_2$NR'$_2$, —SO$_2$OH, —SO$_2$X or —NO$_2$.

For the purposes of the present invention, fully unsaturated substituents are also taken to mean aromatic substituents.

In accordance with the invention, suitable substituents R and $R^2$ to $R^{13}$ of the compounds of the formulae (1) to (4), besides hydrogen, are preferably: $C_1$- to $C_{20}$-, in particular $C_1$- to $C_{14}$-alkyl groups, and saturated or unsaturated, i.e. also aromatic, $C_3$- to $C_7$-cycloaliphatic groups, which may be substituted by $C_1$- to $C_6$-alkyl groups, in particular phenyl.

The substituents R and $R^2$ in the compounds of the formula (1) or (2) may be identical or different. The substituents R and $R^2$ are preferably different.

The substituents R and $R^2$ are particularly preferably methyl, ethyl, isopropyl, propyl, butyl, sec-butyl, pentyl, hexyl, octyl, decyl or tetradecyl.

Up to four substituents of the guanidinium cation $[C(NR^8R^9)(NR^{10}R^{11})(NR^{12}R^{13})]^+$ may also be bonded in pairs in such a way that mono-, bi- or polycyclic cations are formed.

Without restricting generality, examples of such guanidinium cations are:

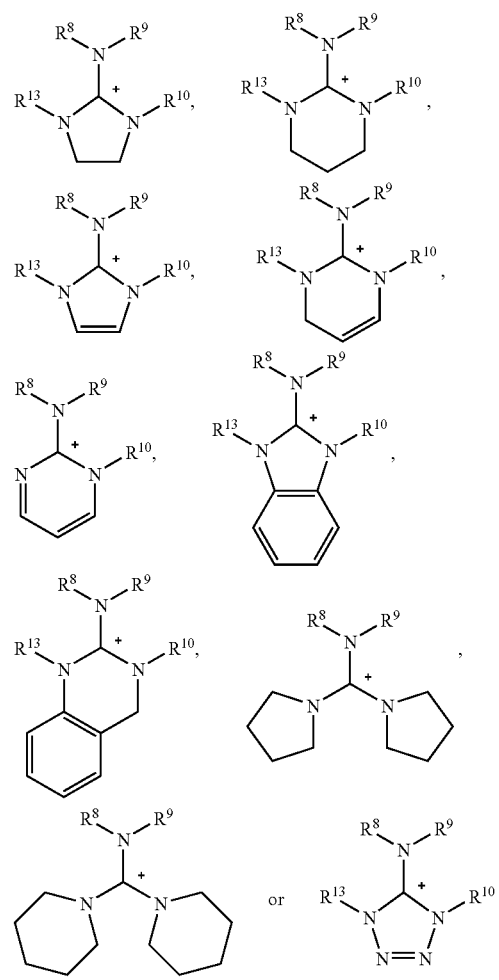

where the substituents $R^8$ to $R^{10}$ and $R^{13}$ can have a meaning or particularly preferred meaning indicated above.

If desired, the carbocyclic or heterocyclic rings of the guanidinium cations indicated above may also be substituted by $C_1$- to $C_6$-alkyl, $C_1$- to $C_6$-alkenyl, NO$_2$, CN, NR'$_2$, F, Cl, Br, I, $C_1$-$C_6$-alkoxy, SCF$_3$, SO$_2$CF$_3$, COOH, SO$_2$NR'$_2$, SO$_2$X' or SO$_3$H, where X and R' have a meaning indicated above, substituted or unsubstituted phenyl or an unsubstituted or substituted heterocycle.

Up to four substituents of the thiouronium cation $[(R^3R^4N)C(=SR^5)(NR^6R^7)]^+$ may also be bonded in pairs in such a way that mono-, bi- or polycyclic cations are formed.

Without restricting generality, examples of such cations are indicated below, where Y=S:

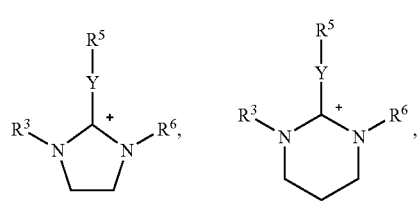

-continued

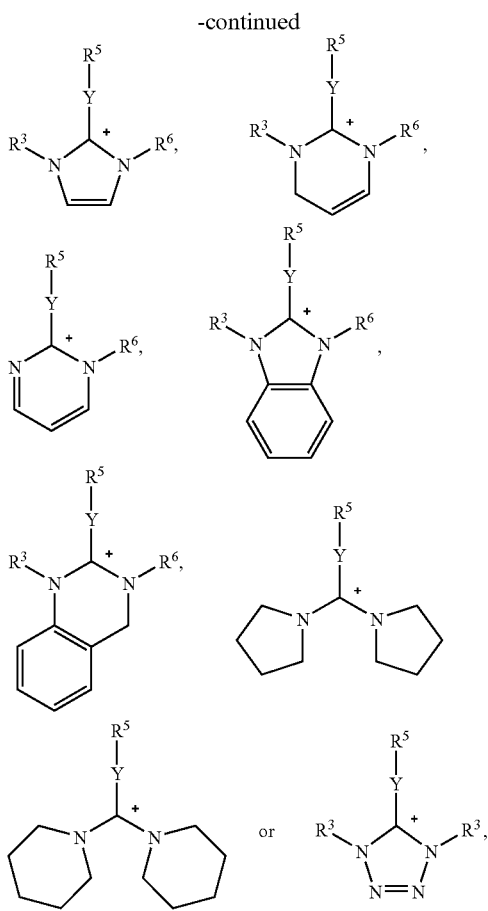

where the substituents $R^3$, $R^5$ and $R^6$ can have a meaning or particularly preferred meaning indicated above.

If desired, the carbocyclic or heterocyclic rings of the cations indicated above may also be substituted by $C_1$- to $C_6$-alkyl, $C_1$- to $C_6$-alkenyl, $NO_2$, CN, $NR'_2$, F, Cl, Br, I, $C_1$-$C_6$-alkoxy, $SCF_3$, $SO_2CF_3$, COOH, $SO_2NR'_2$, $SO_2X$ or $SO_3H$ or substituted or unsubstituted phenyl or an unsubstituted or substituted heterocycle, where X and R' have a meaning indicated above.

The substituents $R^3$ to $R^{13}$ are each, independently of one another, preferably a straight-chain or branched alkyl group having 1 to 10 C atoms. The substituents $R^3$ and $R^4$, $R^6$ and $R^7$, $R^8$ and $R^9$, $R^{10}$ and $R^{11}$ and $R^{12}$ and $R^{13}$ in compounds of the formulae (3) to (4) may be identical or different. $R^3$ to $R^{13}$ are particularly preferably each, independently of one another, methyl, ethyl, n-propyl, isopropyl, n-butyl, tert-butyl, sec-butyl, phenyl or cyclohexyl, very particularly preferably methyl, ethyl, n-propyl, isopropyl or n-butyl.

In accordance with the invention, suitable substituents $R^{1'}$ to $R^{4'}$ of compounds of the formula (5), besides hydrogen, are preferably: $C_1$- to $C_{20}$-, in particular $C_1$- to $C_{12}$-alkyl groups, and saturated or unsaturated, i.e. also aromatic, $C_3$- to $C_7$-cycloaliphatic groups, which may be substituted by $C_1$- to $C_6$-alkyl groups, in particular phenyl.

The substituents $R^{1'}$ and $R^{4'}$ are each, independently of one another, particularly preferably methyl, ethyl, isopropyl, propyl, butyl, pentyl, hexyl, octyl, decyl, cyclohexyl, phenyl or benzyl. They are very particularly preferably methyl, ethyl, n-butyl or hexyl. In pyrrolidinium, piperidinium or indolinium compounds, the two substituents $R^{1'}$ and $R^{4'}$ are preferably different.

The substituent $R^{2'}$ or $R^{3'}$ is in each case, independently of one another, in particular hydrogen, methyl, ethyl, isopropyl, propyl, butyl, sec-butyl, tert-butyl, cyclohexyl, phenyl or benzyl. $R^{2'}$ is particularly preferably hydrogen, methyl, ethyl, isopropyl, propyl, butyl or sec-butyl. $R^{2'}$ and $R^{3'}$ are very particularly preferably hydrogen.

The $C_1$-$C_{12}$-alkyl group is, for example, methyl, ethyl, isopropyl, propyl, butyl, sec-butyl or tert-butyl, furthermore also pentyl, 1-, 2- or 3-methylbutyl, 1,1-, 1,2- or 2,2-dimethylpropyl, 1-ethylpropyl, hexyl, heptyl, octyl, nonyl, decyl, undecyl or dodecyl. Optionally difluoromethyl, trifluoromethyl, pentafluoroethyl, heptafluoropropyl or nonafluorobutyl.

A straight-chain or branched alkenyl having 2 to 20 C atoms, in which a plurality of double bonds may also be present, is, for example, allyl, 2- or 3-butenyl, isobutenyl, sec-butenyl, furthermore 4-pentenyl, isopentenyl, hexenyl, heptenyl, octenyl, —$C_9H_{17}$, —$C_{10}H_{19}$ to —$C_{20}H_{39}$, preferably allyl, 2- or 3-butenyl, isobutenyl, sec-butenyl, furthermore preferably 4-pentenyl, isopentenyl or hexenyl.

A straight-chain or branched alkynyl having 2 to 20 C atoms, in which a plurality of triple bonds may also be present, is, for example, ethynyl, 1- or 2-propynyl, 2- or 3-butynyl, furthermore 4-pentynyl, 3-pentynyl, hexynyl, heptynyl, octynyl, —$C_9H_{15}$, —$C_{10}H_{17}$ to —$C_{20}H_{37}$, preferably ethynyl, 1- or 2-propynyl, 2- or 3-butynyl, 4-pentynyl, 3-pentynyl or hexynyl.

Aryl-$C_1$-$C_6$-alkyl denotes, for example, benzyl, phenylethyl, phenylpropyl, phenylbutyl, phenylpentyl or phenylhexyl, where both the phenyl ring and also the alkylene chain may be partially or fully substituted, as described above, by halogens, in particular —F and/or —Cl, or partially by —OR', —$NR'_2$, —CN, —C(O)OH, —C(O)$NR'_2$, —$SO_2NR'_2$, —C(O)X, —$SO_2OH$, —$SO_2X$, —$NO_2$.

Unsubstituted saturated, partially or fully unsaturated cycloaliphatic groups having 3-7 C atoms are therefore cyclopropyl, cyclobutyl, cyclopentyl, cyclohexyl, cycloheptyl, cyclopentenyl, cyclohexenyl, phenyl, cycloheptenyl, each of which may be substituted by $C_1$- to $C_6$-alkyl groups, where the cycloaliphatic group or the cycloaliphatic group substituted by $C_1$- to $C_6$-alkyl groups may in turn also be substituted by halogen atoms, such as F, Cl, Br or I, in particular F or Cl, or by —OR', —CN, —C(O)OH, —C(O)$NR'_2$, —$SO_2NR'_2$, —$SO_2OH$, —$SO_2X$, —$NO_2$.

In the substituents R, $R^2$ to $R^{13}$ or $R^{1'}$ to $R^{4'}$, one or two non-adjacent carbon atoms which are not bonded in the α-position to the heteroatom may also be replaced by atoms and/or atom groups selected from the group —O—, —S—, —S(O)—, —$SO_2$—, —$N^+R'_2$—, —C(O)NR'—, —$SO_2NR'$— or —P(O)R'—, where R'=non-, partially or perfluorinated $C_1$- to $C_6$-alkyl, $C_3$- to $C_7$-cycloalkyl or unsubstituted or substituted phenyl.

Without restricting generality, examples of substituents R, $R^2$ to $R^{13}$ and $R^{1'}$ to $R^{4'}$ modified in this way are:

—$OCH_3$, —$OCH(CH_3)_2$, —$CH_2OCH_3$, —$CH_2$—$CH_2$—O—$CH_3$, —$C_2H_4OCH(CH_3)_2$, —$C_2H_4C_2H_5$, —$C_2H_4SCH(CH_3)_2$, —$S(O)CH_3$, —$SO_2CH_3$, —$SO_2C_6H_5$, —$SO_2C_3H_7$, —$SO_2CH(CH_3)_2$, —$SO_2CH_2CF_3$, —$CH_2SO_2CH_3$, —O—$C_4H_8$—O—$C_4H_9$, —$CF_3$, —$C_2F_5$, —$C_3F_7$, —$C_4F_9$, —$C(CF_3)_3$, —$CF_2SO_2CF_3$, —$C_2F_4N(C_2F_5)C_2F_5$, —$CHF_2$, —$CH_2CF_3$, —$C_2F_2H_3$, —$C_3H_6$, —$CH_2C_3F_7$, —$C(CFH_2)_3$, —$CH_2C(O)OH$, —$CH_2C_6H_5$ or $P(O)(C_2H_5)_2$.

In R', a $C_3$- to $C_7$-cycloaliphatic radical is, for example, cyclopropyl, cyclobutyl, cyclopentyl, cyclohexyl or cycloheptyl.

In R', substituted phenyl denotes phenyl which is substituted by $C_1$- to $C_6$-alkyl, $C_1$- to $C_6$-alkenyl, $NO_2$, CN, $NR'_2$, F, Cl, Br, I, $C_1$-$C_6$-alkoxy, $SCF_3$, $SO_2CF_3$, COOH, $SO_2X'$, $SO_2NR'_2$ or $SO_3H$, where X' denotes F, Cl or Br, and R'' denotes a non-, partially or perfluorinated $C_1$- to $C_6$-alkyl or $C_3$- to $C_7$-cycloalkyl as defined for R', for example o-, m- or p-methylphenyl, o-, m- or p-ethylphenyl, o-, m- or p-propylphenyl, o-, m- or p-isopropylphenyl, o-, m- or p-tert-butylphenyl, o-, m- or p-nitrophenyl, o-, m- or p-methoxyphenyl, o-, m- or p-ethoxyphenyl, o-, m-, p-(trifluoromethyl) phenyl, o-, m-, p-(trifluoromethoxy)phenyl, o-, m-, p-(trifluoromethylsulfonyl)phenyl, o-, m- or p-fluorophenyl, o-, m- or p-chlorophenyl, o-, m- or p-bromophenyl, o-, m- or p-iodophenyl, furthermore preferably 2,3-, 2,4-, 2,5-, 2,6-, 3,4- or 3,5-dimethylphenyl, 2,3-, 2,4-, 2,5-, 2,6-, 3,4- or 3,5-dihydroxyphenyl, 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,3-, 2,4-, 2,5-, 2,6-, 3,4- or 3,5-dimethoxyphenyl, 5-fluoro-2-methylphenyl, 3,4,5-trimethoxyphenyl or 2,4,5-trimethylphenyl.

In $R^{1'}$ to $R^{4'}$, heteroaryl is taken to mean a saturated or unsaturated mono- or bicyclic heterocyclic radical having 5 to 13 ring members, in which 1, 2 or 3 N and/or 1 or 2 S or O atoms may be present and the heterocyclic radical may be mono- or polysubstituted by $C_1$- to $C_6$-alkyl, $C_1$- to $C_6$-alkenyl, $NO_2$, CN, $NR'_2$, F, Cl, Br, I, $C_1$-$C_6$-alkoxy, $SCF_3$, $SO_2CF_3$, COOH, $SO_2X'$, $SO_2NR'_2$ or $SO_3H$, where X' and R' have a meaning indicated above.

The heterocyclic radical is preferably substituted or unsubstituted 2- or 3-furyl, 2- or 3-thienyl, 1-, 2- or 3-pyrrolyl, 1-, 2-, 4- or 5-imidazolyl, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -4- or -5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 2-, 3-, 4-, 5- or 6-2H-thiopyranyl, 2-, 3- or 4-4H-thiopyranyl, 3- or 4-pyridazinyl, pyrazinyl, 2-, 3-, 4-, 5-, 6- or 7-benzofuryl, 2-, 3-, 4-, 5-, 6- or 7-benzothienyl, 1-, 2-, 3-, 4-, 5-, 6- or 7-1H-indolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 1-, 2-, 3-, 4-, 5-, 6-, 7- or 8-quinolinyl, 1-, 3-, 4-, 5-, 6-, 7- or 8-isoquinolinyl, 1-, 2-, 3-, 4- or 9-carbazolyl, 1-, 2-, 3-, 4-, 5-, 6-, 7-, 8- or 9-acridinyl, 3-, 4-, 5-, 6-, 7- or 8-cinnolinyl, 2-, 4-, 5-, 6-, 7- or 8-quinazolinyl or 1-, 2- or 3-pyrrolidinyl.

Heteroaryl-$C_1$-$C_6$-alkyl is, analogously to aryl-$C_1$-$C_6$-alkyl, taken to mean, for example, pyridinylmethyl, pyridinylethyl, pyridinylpropyl, pyridinylbutyl, pyridinylpentyl or pyridinylhexyl, where the heterocyclic radicals described above may furthermore be linked to the alkylene chain in this way.

HetN⁺ is preferably

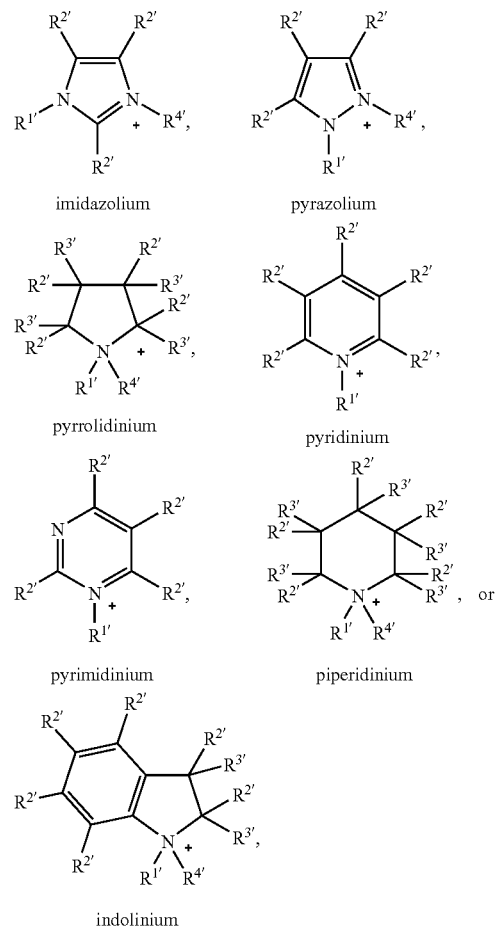

where the substituents $R^{1'}$ to $R^{4'}$ each, independently of one another, have a meaning described above.

The cations of the ionic liquid according to the invention are preferably ammonium, phosphonium, imidazolium, pyridinium or pyrrolidinium cations.

Particularly preferred ionic liquids are ammonium, phosphonium, imidazolium or pyrrolidinium hydrogensulfates, alkylsulfates, alkylsulfonates, perfluoroalkylsulfonates, phosphates, hydrogenphosphates, alkylphosphates, alkyl- and perfluoroalkylphosphinates, alkyl- and perfluoroalkylphosphonates or perfluoroalkylcarboxylates.

The reaction according to the invention can be summarised in the following reaction scheme:

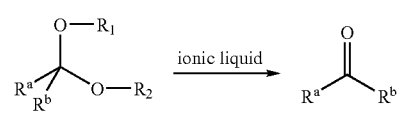

In a further preferred embodiment of the process according to the invention, the at least one ionic liquid additionally comprises at least one acid, preferably an acid corresponding to the anion A⁻. In general, any acid is suitable for mixing with the ionic liquid. Examples of preferred mixtures which prove to be particularly suitable in the processes according to the invention are, for example, mixtures of ionic liquids containing [HSO$_4$]$^-$ anions and H$_2$SO$_4$. Alternative examples are mixtures of ionic liquids containing [CF$_3$SO$_3$]$^-$ anions and CF$_3$SO$_3$H or mixtures of ionic liquids containing [CF$_3$C(O)O]$^-$ anions and CF$_3$C(O)OH. The said mixtures should be regarded as illustrative here without representing a limitation of the possibilities of the present invention.

The proportion of acid in the ionic liquid can be 0 to 90% by weight, based on the mixture, preferably in the range from 0 to 50% by weight.

The process temperature is not crucial per se and is usually 0° C. to 170° C., preferably 20° C. to 120° C.

The said mixtures of ionic liquids and at least one acid are particularly suitable in the processes according to the invention since the ketal cleavage or acetal cleavage proceeds more quickly than with the ionic liquid alone. In addition, it has been found that, in particular, mixtures of ionic liquids and acids corresponding to the anion A$^-$ of the ionic liquid are distinguished by the fact that the acid has low volatility in the mixture, i.e. is present in the mixture in constant concentration, even at elevated temperatures. Thus, for example, trifluoroacetic acid proves to be virtually non-volatile and has only a low vapour pressure in the mixture with an ionic liquid containing a trifluoroacetate anion.

The process according to the invention is particularly advantageously employed for the synthesis of aryl-substituted aldehydes or ketones, which are used, for example, as mesogenic substances, pharmaceutical active compounds, crop-protection agents, polymers or precursors in fine chemistry or for the preparation of corresponding starting compounds.

It is self-evident to the person skilled in the art that substituents such as, for example, H, N, O, Cl, F in the said ionic liquids or compounds of the formula (I) may be replaced by the corresponding isotopes.

The following working examples are intended to explain the invention without limiting it. Above and below, percentage data denote percent by weight. All temperatures are indicated in degrees Celsius.

EXAMPLES

Example 1

Synthesis of cyclohex-1-one

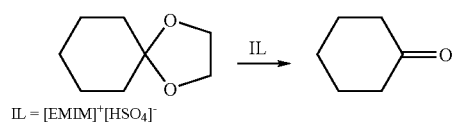

IL = [EMIM]$^+$[HSO$_4$]$^-$ 15.5 g (109.0 mmol) of cyclohexanone ethylene ketal are added to 50 ml of 1-ethyl-3-methylimidazolium hydrogensulfate in a 100 ml round-bottomed flask, and the mixture is stirred at 90-100° C. for half an hour. The volatile constituents are then distilled off at a pressure of 35 mbar using a Vigreux column (20 cm) over the course of 4 hours. 5.58 g of a clear and colourless liquid are isolated, which separates over time. The lower (2.14 g) of the two phases consists of a solution of pure cyclohexanone and acid and is returned to the ionic liquid.

The upper phase (3.44 g) comprises cyclohexanone, C$_6$H$_{10}$O (purity 97%). A further 22.4 g (157.5 mmol) of cyclohexanone ethylene ketal, C$_8$H$_{14}$O$_2$, are added to the ionic liquid (emulsion) remaining, and the mixture is stirred again for one hour at 90-100° C. After distillation for 2 hours at a pressure of 35 mbar, a clear and colourless liquid (7.21 g) is isolated, which separates over time. The lower (3.00 g) of the two phases consists of pure cyclohexanone and acid and is returned to the ionic liquid. The upper phase (3.44 g) comprises cyclohexanone, C$_6$H$_{10}$O (purity 96%), which is separated off. On further distillation in vacuo (5 mbar), further distillate (12.2 g) of two substances: cyclohexanone ethylene ketal, C$_8$H$_{14}$O$_2$ (50 mol %) and cyclohexanone, C$_6$H$_{10}$O (50 mol %), can be obtained. Cyclohexanone can be isolated from this distillate in a further step. Sulfuric acid must subsequently be added to the reaction mixture in order to carry out further reactions.

This operation can be repeated a number of times without changing the ionic liquid.

The product, cyclohexanone, is characterised by means of NMR spectroscopy.

Cyclohexanone:
$^1$H-NMR (reference: TMS; solvent: CD$_3$CN), ppm: 1.64 m (2H); 1.79 m (4H); 2.26 m (4H). $^{13}$C {$^1$H} NMR (reference: TMS; solvent: CD$_3$CN), ppm: 25.9 s (CH$_2$); 28.1 s (2CH$_2$); 42.7 s (2CH$_2$); 211.0 s (C=O)

Example 2

Synthesis of Acetone

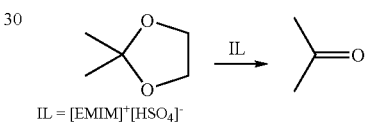

IL = [EMIM]$^+$[HSO$_4$]$^-$ 3.54 g (34.7 mmol) of 2,2-dimethyl-1,3-dioxolane are added to 3 ml of 1-ethyl-3-methylimidazolium hydrogensulfate in a 25 ml round-bottomed flask, and the mixture (emulsion) is stirred at 70° C. for six hours. All volatile constituents are then pumped off at $10^{-2}$ mbar and 85-90° C. and frozen in a cold trap at −196° C. After work-up, 1.92 g of acetone having a purity of 92% are obtained. The yield of acetone is 88%.

Acetone:
$^1$H NMR (reference: TMS; solvent: CD$_3$CN), ppm: 2.09 s (6H) $^{13}$C{$^1$H} NMR (reference: TMS; solvent: CD$_3$CN), ppm: 31.1 s (CH$_3$), 206.9 s (CO).

This operation can be repeated a number of times without changing the ionic liquid.

Comparable results are obtained on use of a mixture of EMIM hydrogensulfate and 0.5 mol of H$_2$SO$_4$ (based on the starting compound).

Example 3

Synthesis of Acetaldehyde

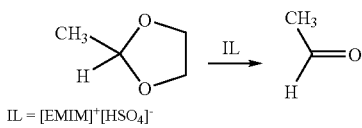

IL = [EMIM]$^+$[HSO$_4$]$^-$ 1.49 g (16.9 mmol) of 2-methyl-1,3-dioxolane are added to 3 ml of 1-ethyl-3-methylimidazolium hydrogensulfate in a 25 ml round-bottomed flask, and the mixture (emulsion) is stirred at 64° C. for six hours. All volatile constituents are then pumped off at $10^{-2}$ mbar and 85-90° C. and frozen in a cold trap at −196° C. After warming to room temperature, 0.84 g of a colourless liquid is obtained. According to $^1$H NMR spectroscopy, the distillate comprises two compounds, namely 2-methyl-1,3-dioxolane (about 13 mol %) and acetaldehyde (about 87 mol %). The product, acetaldehyde, can be purified by fractional distillation.

Acetaldehyde:

$^1$H NMR (reference: TMS; solvent: CD$_3$CN), ppm: 2.10 d (CH$_3$); 9.68 q (CHO); $^3J_{HH}$=2.9 Hz. $^{13}$C{$^1$H} NMR (reference: TMS; solvent: CD$_3$CN), ppm: 31.1 s (CH$_3$); 201.1 s (CHO).

This operation can be repeated a number of times without changing the ionic liquid.

Comparable results are obtained on use of a mixture of EMIM hydrogensulfate and 0.5 mol of H$_2$SO$_4$ (based on the starting compound), where the product of the aldol reaction, principally 3-methylacrolein, is additionally found in the reaction mixture.

Example 4

Synthesis of Acetone

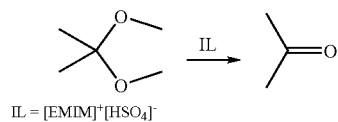

IL = [EMIM]$^+$[HSO$_4$]$^-$ 3.81 g (36.5 mmol) of 2,2-dimethoxypropane are added to 6 ml of 1-ethyl-3-methylimidazolium hydrogensulfate in a 25 ml round-bottomed flask, and the mixture (emulsion) is stirred at 55-60° C. for six hours. All volatile constituents are then distilled off at 1 mbar and 55-60° C. and frozen in a cold trap at −196° C. After warming to room temperature, 3.38 g of a colourless liquid are obtained. According to $^1$H NMR spectroscopy, the distillate comprises two compounds, acetone (about 62 mol %) and dimethyl ether (about 38 mol %). The product, acetone, is purified by fractional distillation and characterised by means of NMR spectroscopy.

Acetone:

$^1$H NMR (reference: TMS; solvent: CD$_3$CN), ppm: 2.04 s $^{13}$C {$^1$H} NMR (reference: TMS; solvent: CD$_3$CN), ppm: 30.8 s (CH$_3$), 206.6 (CO).

Dimethyl Ether:

$^1$H NMR (reference: TMS; solvent: CD$_3$CN), ppm: 3.30 s. $^{13}$C {$^1$H} NMR (reference: TMS; solvent: CD$_3$CN), ppm: 49.8 s (CH$_3$).

This operation can be repeated a number of times without changing the ionic liquid.

What is claimed is:

1. A process for the cleavage of dialkoxyalkanes of to give aldehydes or ketones, comprising cleaving a compound of formula I:

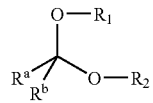

where $R^a$ and $R^b$, independently of one another, denote an optionally substituted aliphatic or aromatic radical, which may have one or more heteroatoms, where one of the radicals $R^a$ or $R^b$ may also denote H, and where the two radicals $R^a$ and $R^b$ may be connected to one another, and where $R_1$ and $R_2$, independently of one another, denote an optionally substituted saturated or unsaturated aliphatic or aromatic radical, which may have one or more heteroatoms, and where the two radicals $R_1$ and $R_2$ may be connected to one another, in the presence of at least one ionic liquid of the general formula K$^+$A$^-$, wherein anion A− of the ionic liquid is [HSO$^4$]—, [SO$^4$]$^{2-}$, [NO$_3$]—, [BF$_4$]—, [(R$_F$)BF$_3$]—, [(R$_F$)$_2$BF$_2$]—, [(R$_F$)$_3$BF]—, [(R$_F$)$_4$B]—, [B(CN)$_4$]—, [PO$_4$]$^{3-}$, [HPO$_4$]$^{2-}$, [H$_2$PO$_4$]—, [alkyl-OPO$_3$]$^{2-}$, [(alkyl-O)$_2$PO$_2$]—, [alkyl-PO$_3$]$^{2-}$, [R$_F$PO$_3$]$^{2-}$, [(alkyl)$_2$PO$_2$]—, [(R$_F$)$_2$PO$_2$]—, [R$_F$SO$_3$]—, [HOSO$_2$(CF$_2$)$_n$SO$_2$O]—, [OSO$_2$(CF$_2$)$_n$SO$_2$O]$^{2-}$, [alkyl-SO$_3$]—, [HOSO$_2$(CH$_2$)$_n$SO$_2$O]—, [OSO$_2$(CH$_2$)$_n$SO$_2$O]$^{2-}$, [alkyl-OSO$_3$]—, [alkyl-C(O)O]—, [HO(O)C(CH$_2$)$_n$C(O)O]—, [R$_F$C(O)O]—, [HO(O)C(CF$_2$)$_n$C(O)O]—, [O(O)C(CF$_2$)$_n$C(O)O]$^{2-}$, [(R$_F$SO$_2$)$_2$N]—, [(FSO$_2$)$_2$N]—, [((R$_F$)$_2$P(O))$_2$N]—, [(R$_F$SO$_2$)$_3$C]—, [(FSO$_2$)$_3$C]—, Cl— and/or Br—, where n=1 to 8, and $R_F$ is fluorinated alkyl of the formula $(C_mF_{2m-x+1}H_x)$ where m=1-12 and x=0-7, where, for m=1, x must be 0 to 2, and/or fluorinated aryl or alkylaryl.

2. The process according to claim 1, wherein the cations K$^+$ of the ionic liquid are ammonium, phosphonium, thiouronium, guanidinium or heterocyclic cations.

3. The process according to claim 1, wherein the at least one ionic liquid additionally comprises an acid corresponding to the anion A$^-$.

4. The process according to claim 3, having a proportion of acid in the ionic liquid of 0 to 90% by weight, based on the mixture.

5. The process according to claim 1, conducted at a process temperature of 0° C. to 170° C.

6. The process according to claim 1, wherein $R^a$ has formula Ia

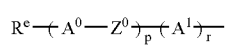

in which $R^e$ denotes an alkyl radical having 1 to 15 C atoms which is unsubstituted, mono- or polysubstituted by CN and/or halogen, where, in addition, one or more CH$_2$ groups may be replaced by —O—, —S—, —CH═CH—, —C≡C—, —OC—O— and/or —O—CO—, and/or, in addition, one or more CH groups in these radicals may be replaced by N or P in such a way that two O atoms are not linked directly to one another, or, if r and/or p are different from 0, also denotes H, halogen, CN, SF$_5$ or NCS, $A^0$, $A^1$ each, independently of one another, denote
  a) a 1,4-cyclohexenylene or 1,4-cyclohexylene radical, in which one or two non-adjacent $CH_2$ groups may be replaced by —O— or —S—,
  b) a 1,4-phenylene radical, in which one or two CH groups may be replaced by N,
  c) piperidine-1,4-diyl, 1,4-bicyclo[2.2.2]-octylene, phenanthrene-2,7-diyl, naphthalene-2,6-diyl, decahydronaphthalene-2,6-diyl and 1,2,3,4-tetrahydronaphthalene-2,6-diyl,
  d) furan, pyrrole, thiophene, pyrazole, imidazole, 1,2-oxazole, 1,3-oxazole, thiazole, pyridine, pyridazine, pyrimidine, pyrazine, 2H-pyran, 4H-pyran, purine, pteridine, 1H-azepine, 3H-1,4-diazepine, indole, benzofuran, benzothiophene, quinoline, isoquinoline, phenazine, phenoxazine, phenothiazine and 1,4-benzodiazepine, where a), b), c) and d) may be mono- or polysubstituted by $R^e$, $Z^0$ denotes —CO—O—, —O—CO—, —$CF_2$O—, —O$CF_2$—, —$CH_2$O—, —O$CH_2$—, —$_{CH2}CH_2$—, —$(CH_2)_4$—, —$C_2F_4$—, —$CH_2CF_2$—, —$CF_2CH_2$-, —CF=CF—, —CH=CH—, —C≡C— or a single bond, p denotes 0, 1, 2 or 3, and r denotes 0, 1 or 2.

7. The process according to claim 6, wherein the radical $R^b$ denotes H.

8. The process according to claim 6, wherein $R^e$ is halogen and/or CN.

* * * * *